United States Patent

Shibanuma et al.

[11] Patent Number: 5,849,658
[45] Date of Patent: Dec. 15, 1998

[54] METHOD FOR PREPARING FLUORINATION CATALYST USED TO FLUORINATE HALOGENATED HYDROCARBONS

[75] Inventors: Takashi Shibanuma; Yoshio Iwai; Satoshi Koyama, all of Osaka, Japan

[73] Assignee: Daikin Industries Ltd., Osaka, Japan

[21] Appl. No.: 435,166

[22] Filed: May 5, 1995

Related U.S. Application Data

[63] Continuation of Ser. No. 52,684, Apr. 27, 1993, which is a continuation-in-part of Ser. No. 886,822, May 22, 1992, abandoned.

[30] Foreign Application Priority Data

May 24, 1991 [JP] Japan .................... 2-120132

[51] Int. Cl.$^6$ .................... B01J 27/132
[52] U.S. Cl. .................... 502/228; 502/224; 502/305; 502/319
[58] Field of Search .................... 502/224, 228, 502/305, 319; 570/168

[56] References Cited

U.S. PATENT DOCUMENTS

| | | |
|---|---|---|
| 2,745,886 | 5/1956 | Ruh et al. . |
| 2,885,427 | 5/1959 | Ruh et al. . |
| 3,426,009 | 2/1969 | Chapman et al. . |
| 3,644,545 | 2/1972 | Buckman . |
| 3,755,477 | 8/1973 | Firth et al. .................... 570/165 |
| 4,158,675 | 6/1979 | Potter . |
| 4,311,863 | 1/1982 | Gumprecht . |
| 4,439,534 | 3/1984 | Foulletier . |
| 4,748,285 | 5/1988 | Foulletier . |
| 4,766,259 | 8/1988 | Manzer et al. . |
| 4,792,643 | 12/1988 | Sobolev . |
| 4,828,818 | 5/1989 | Carlson et al. . |
| 4,876,406 | 10/1989 | Foulletier . |
| 4,912,270 | 3/1990 | Carlson et al. . |
| 5,334,786 | 8/1994 | Koyama et al. .................... 570/168 |
| 5,494,876 | 2/1996 | Tsuji et al. .................... 502/224 |
| 5,500,400 | 3/1996 | Kim et al. .................... 502/306 |

FOREIGN PATENT DOCUMENTS

| | | |
|---|---|---|
| 0055652 | 7/1982 | European Pat. Off. . |
| 0055958 | 7/1982 | European Pat. Off. . |
| 1091103 | 11/1967 | United Kingdom . |
| 1307224 | 2/1973 | United Kingdom . |

*Primary Examiner*—Elizabeth D. Wood
*Attorney, Agent, or Firm*—Birch, Stewart, Kolasch & Birch, LLP

[57] ABSTRACT

A method for preparing a fluorination catalyst is disclosed, wherein the catalyst contains chromium oxide, has a specific surface area of from 170 m$^2$g to 300 m$^2$/g, catalyzes the fluorination of a halogenated hydrocarbon with hydrogen fluoride, and has a high activity and long catalyst life. The method includes mixing an aqueous solution of a chromium salt with aqueous ammonia to precipitate chromium hydroxide, drying the precipitated chromium hydroxide, sintering the dried chromium hydroxide, and fluorinating the sintered chromium hydroxide to obtain the chromium oxide catalyst.

8 Claims, 3 Drawing Sheets

METHOD FOR PREPARING FLUORINATION CATALYST USED TO FLUORINATE HALOGENATED HYDROCARBONS

This application is a continuation of application Ser. No. 08/052,684 filed on Apr. 27, 1993, which is a Continuation-in-Part of Ser. No. 07/886,822 filed May 22, 1992, which is now abandoned, the entire contents of which are hereby incorporated by reference.

BACKGROUND OF THE INVENTION

1. Field of the Invention

The present invention relates to a fluorination catalyst and a process for fluorinating a halogenated hydrocarbon in a gas phase in the presence of the fluorination catalyst.

2. Description of the Related Art

Fluorinated halohydrocarbons such as 1,1,1,2-tetrafluoroethane are useful as substitutes for fluorocarbons and used as a refrigerant, a blowing agent, a propellant, a cleaning agent, and the like.

As a fluorination catalyst, chromium oxide which may be supported on alumina is known (see Japanese Patent Publication Nos. 10310/1964, 3004/1967 and 44973/ 1987, U.S. Pat. Nos. 3,426,009, 3,755,477 and 4,158,675 and GB 1 589 924). Also, fluorination in the presence of a chromium salt or partially fluorinated chromium oxide which may be supported on a carrier is known (see U.S. Pat. Nos. 2,745,886 and 2,885,427, DE Patent No. 1 252 182, Japanese Patent Publication No. 54503/1976, Japanese Patent Kokai Publication No. 132549/1978 and WO89/10341).

A catalyst comprising chromium oxide and an additive such as NaF (U.S. Pat. No. 3,644,545), Mg or Ba (Japanese Patent Publication No. 43922/1974), a transition metal (U.S. Pat. No. 4,792,643) or AlPO$_4$ (Japanese Patent Publication No. 17413/1989) is also known. Further, processes are known which use a catalyst comprising metal chromium (Japanese Patent Kokai Publication Nos. 19038/1985 and 221338/1989) or a metal other than chromium (Japanese Patent Kokai Publication Nos. 186945/1987, 268651/1989, 172933/1990 and 95438/1990).

U.S. Pat. No. 4,766,259 discloses a fluorination reaction using partially fluorinated aluminum oxide.

A liquid phase fluorination reaction using a Sb catalyst is known. In addition, a liquid phase fluorination reaction using an alkali metal fluoride as a catalyst is known (see U.S. Pat. No. 4,311,863 and Japanese Patent Kokai Publication No. 228925/1989).

As the halogenated hydrocarbons, various compounds are used. The fluorination is explained by making reference to preparation of 1,1,1,2-tetrafluoroethane (hereinafter referred to as "134a") by the fluorination of trichloroethylene or 1,1,1-tetrafluorochloroethane (hereinafter referred to as "133a").

It is not advantageous to synthesize 134a from 133a by a liquid phase reaction in view of the low conversion and the material of the reactor. When this fluorination reaction is carried out in the gas phase, conversion of 133a to 134a is low due to equilibrium. Therefore, a catalyst to be used should catalyze this reaction at a relatively low conversion and have a sufficiently long life and a good selectivity for industrial use. Prolongation of the catalyst life avoids frequent change of the catalyst and lowers the catalyst cost.

The catalyst life can be prolonged by the addition of chlorine gas (Japanese Patent Publication No. 33604/1977) or oxygen gas (GB Patent No. 2 030 981 and Japanese Patent Kokai Publication Nos. 82206/1976 and 272535/1989) to the reaction gas mixture. When the chlorine gas is added, selection of the material of the reactor may be limited and also an increase in by-products must be considered. When the oxygen gas is added, the conversion may be decreased.

In view of the above, it is advantageous to provide a catalyst which has a long life as such. When such a catalyst is excellent in catalytic activity, not only the catalyst cost but also the size of the reactor, which is made of high quality expensive material, can be reduced advantageously.

SUMMARY OF THE PRESENT INVENTION

One object of the present invention is to provide a novel fluorination catalyst which can effectively catalyze the fluorination of a halogenated hydrocarbon.

Another object of the present invention is to provide a process for fluorinating a halogenated hydrocarbon in the gas phase.

According to a first aspect of the present invention, there is provided a fluorination catalyst comprising chromium oxide having a specific surface area of from 170 m$^2$/g to 300 m$^2$/g.

According to a second aspect of the present invention, there is provided a process for fluorinating a halogenated hydrocarbon in the presence of the above fluorination catalyst of the present invention.

DETAILED DESCRIPTION OF THE INVENTION

Figure 1A:
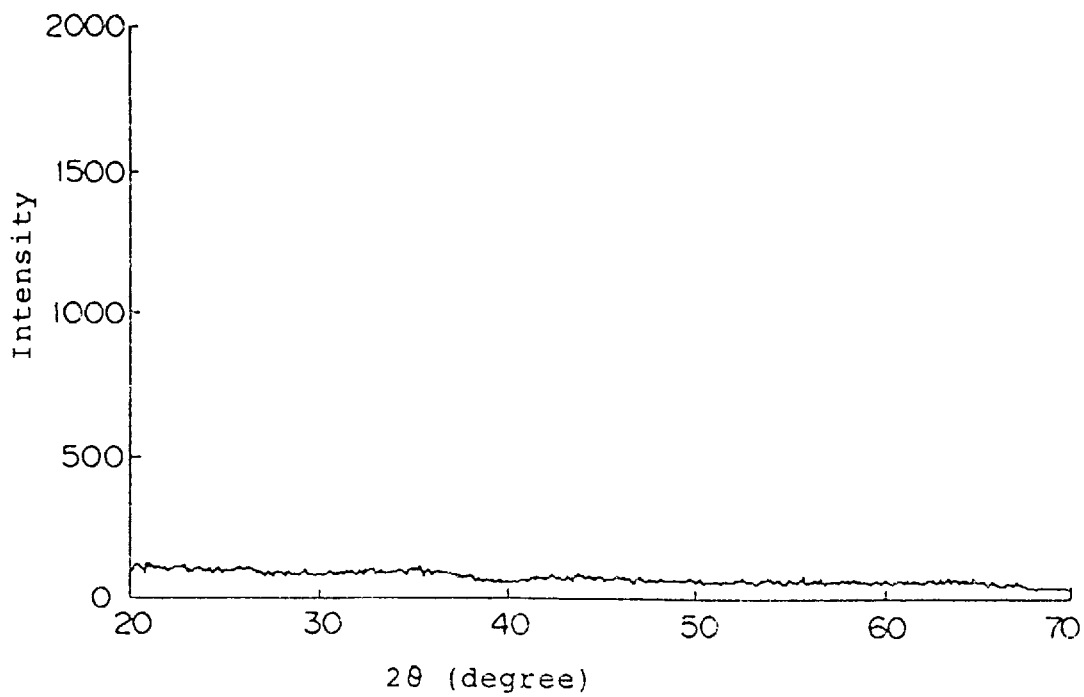
FIGS. 1A and 1B are x-ray diffraction patterns of amorphous chromium oxide and crystalline chromium oxide respectively.

Chromium oxide which is used as the catalyst according to the present invention is preferably amorphous. Herein, "amorphous" is intended to mean that there is no substantial peak in an x-ray diffraction pattern of the chromium oxide.

Preferably chromium oxide is partially fluorinated.

In the present invention, with the control of properties of the catalyst in the preparation steps, a fluorination catalyst having a high activity and a long life, namely high productivity in comparison to the conventional catalysts, can be produced. The catalyst may be activated with an oxygen-containing gas such as air.

In a preferred embodiment, the composition of chromium oxide is as follows:

When chromium oxide is expressed by the formula: Cr$_2$O$_3$.nH$_2$O, n is not larger than 3, preferably from 1 to 1.5. In chromium oxide, an atomic ratio of oxygen to chromium is not larger than 3:1, preferably from 2:1 to 2.75:1, more preferably from 2:1 to 2.3:1.

The chromium oxide catalyst of the present invention may be prepared as follows:

First, an aqueous solution of a chromium salt (e.g. chromium nitrate, chromium chloride, chrome alum, chromium sulfate, etc.) and aqueous ammonia are mixed to precipitate chromium hydroxide. For example, to a 5.7% aqueous solution of chromium nitrate, 1 to 1.2 times equivalent of 10% aqueous ammonia is added dropwise. Properties of chromium hydroxide can be controlled by adjusting the reaction rate of the precipitation reaction. The higher reaction rate, the better. The reaction rate depends on the temperature of the reaction system, the method of mixing the aqueous ammonia (i.e. a mixing speed), the stirring conditions, etc.

Precipitated chromium hydroxide is dried, for example, in air, at a temperature of 70° to 200° C., in particular around 120° C., for 1 to 100 hours, in particular around 12 hours. The catalyst at this stage is referred to as a "chromium hydroxide state catalyst". This catalyst is powdered to 1 mm or smaller. The amount of powder having a particle size of 46 to 1000 μm is preferably about 95%.

The precipitation reaction rate is adjusted so that the powder density is from 0.6 to 1.1 g/ml, preferably from 0.6 to 1.0 g/ml. When the powder density is smaller than 0.6 g/ml, the strength of a pellet produced from the powder is not sufficient. When the powder density is larger than 1.1 g/ml, the catalyst has low activity.

The specific surface area of the powder is at least 100 m$^2$/g, preferably at least 120 m$^2$/g after degassing at 200° C. for 80 minutes. The upper limit of the specific surface area of the powder is preferably 220 m$^2$/g.

The chromium hydroxide powder which contains optionally 3% by weight or less of graphite is pelletized by each pelletizer. Preferably, a pellet has a diameter of 3.0 mm and a height of 3.0 mm, and a crushing pressure (i.e. strength of the pellet) of 210±40 Kg/cm. When the crushing pressure is too large, the contact efficiency of the gas and also the catalytic activity decrease, and the pellet tends to be easily cracked. When the crushing pressure is too small, the pellet is easily powdered so that handleability of the pellet is deteriorated.

The formed catalyst is then sintered in an atmosphere of an inert gas, for example, in a stream of nitrogen to obtain amorphous chromium oxide. The sintering temperature is usually at least 360° C. But, since too high of a sintering temperature will crystallize chromium oxide, the sintering temperature should be as high as possible in a temperature range in which the chromium oxide is not crystallized. Preferably, the sintering is carried out at a temperature of 380° to 460° C., in particular around 400° C. for 1 to 5 hours, in particular around 2 hours.

The sintered catalyst has a specific surface area of from 170 m$^2$/g to 300 m$^2$/g, preferably from 180 m$^2$/g to 280 m$^2$/g, more preferably from 200 m$^2$/g to 260 m$^2$/g. When the specific surface area is smaller than 170 m$^2$/g, the catalyst has an insufficient activity. As the surface area of the catalyst increases, the catalytic activity increases. But, above 300 m$^2$/g, the catalytic activity saturates. Preferably, the specific surface area does not exceed 280 m$^2$/g.

In the present invention, the specific surface area of chromium oxide catalyst is measured using "MONOSORB" (manufactured by Quanta Chrome).

The catalyst is preferably fluorinated, namely treated with hydrogen fluoride. The fluorination is carried out at a temperature at which water is not condensed, for example around 150° C. under a pressure of one atmosphere but not higher than the temperature at which the catalyst is not crystallized by the reaction heat. Preferably, the fluorination temperature is from 100° to 460° C. The pressure is not limited. The same pressure as in the catalytic reaction is preferable.

When the catalyst is not fluorinated, hydrogen fluoride will react with the catalyst and the desired reaction is greatly inhibited.

The fluorination of the catalyst is effected till the content of fluorine in the catalyst reaches at least 8% by weight. In order to prevent the inhibition of the desired reaction, the fluorine content is preferably at least 15% by weight. The upper limit of the fluorine content is usually 48% by weight. The specific surface area of the catalyst may be decreased by the fluorination.

By the process of the present invention, various halogenated hydrocarbons can be fluorinated. Specific examples of the halogenated hydrocarbon are trichloroethylene, 1,1,1-trifluorochloroethane (133a), carbon tetrachloride, chloroform, dichloromethane, chloromethane, 1,1,1-trichloroethane, trichlorotrifluoroethane (113a, 113), $CF_3CHCl_2$ (123), $CF_3CHClF$ (124), perchloroethylene ($CCl_2$=$CCl_2$), and the like.

The products obtained by the process of the present invention are as follows:

1,1,1,2-tetrafluoroethane (134a) from 1,1,1-trifluorochloroethane,
114 from $CCl_2$=$CCl_2$ or 113,
115 from $CCl_2$=$CCl_2$, 113, 113a or 114a,
124 from $CCl_2$=$CCl_2$ or 123,
125 from $CCl_2$=$CCl_2$, 123 or 124,
32 from dichloromethane or chlorofluoromethane,
41 from chloromethane,
11 from carbon tetrachloride,
12 from carbon tetrachloride or trichloromethane,
141b from 1,1,1-trichloroethane,
142b from 1,1,1-trichloroethane or 141b,
143a from 1,1,1-trichloroethane, 141b or 142b.

One example of the reactions which occur in the process of the present invention is:

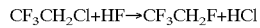

$$CF_3CH_2Cl + HF \rightarrow CF_3CH_2F + HCl$$

A molar ratio of hydrogen fluoride to the halogenated hydrocarbon and the reaction temperature are selected according to the characteristics of each reaction. In general, the molar ratio of hydrogen fluoride to the halogenated hydrocarbon is from 0.9:1 to 16:1. The reaction temperature is usually from 80° to 450° C. A preferred reaction pressure depends on the kind of reaction.

For example, in the reaction for preparing 134a from 133a, the conversion and the catalyst life can be adjusted by changing the molar ratio of hydrogen fluoride to 133a and changing the reaction temperature. A preferred molar ratio of hydrogen fluoride to 133a is from 0.9:1 to 10:1, and a preferred reaction temperature is from 290° to 380° C. The reaction pressure is preferably atmospheric pressure. Under elevated pressure, the catalyst activity may decrease.

PREFERRED EMBODIMENTS OF THE INVENTION

The present invention will be explained further in detail by following examples.

In following Examples 1–8 and Comparative Examples 1–5, 133a was fluorinated with hydrogen fluoride to prepare 134a.

As a reactor tube, a Hasteloy C tube having an inner diameter of 15 mm was used.

In Examples 1–3 and Comparative Examples 1–3, the catalyst was pelletized and ground to a powder having a particle size of 300 to 1000 μm.

In the Examples and Comparative Examples, catalytic activity, selectivity, catalyst life and throughput were compared. Unless otherwise defined, the catalytic activity, the catalyst life and the throughput are defined as follows:

The catalytic activity is the achieved maximum conversion (%).

The catalyst life is the time (hr) at which the conversion decreased to 60% of the maximum value.

The throughput is the amount of the reaction product (134a) produced per one liter of the catalyst per one hour.

EXAMPLE 1

To a 5.7% aqueous solution of chromium nitrate (765 Kg), 10% aqueous ammonia (114 Kg) was added over 2 minutes 10 seconds. The precipitate was collected by filtration and dried in air at 120° C. for 12 hours to obtain chromium hydroxide. Chromium oxide was molded to obtain pellets each having a diameter of 3.0 mm and a height of 3.0 mm and sintered at 400° C. for 2 hours to obtain amorphous chromium oxide. Then, amorphous chromium oxide was fluorinated with hydrogen fluoride at 200° C. for 2 hours to obtain a catalyst having a fluorine content of 15.6% by weight.

Chromium hydroxide and amorphous chromium oxide had the following properties:

Chromium hydroxide

Powder density: 0.80 g/ml

Pellet strength: 241 kg/cm$^2$

Specific surface area: 180 m$^2$/g

Chromium oxide

Specific surface area: 241 m$^2$/g

Figure 1B:
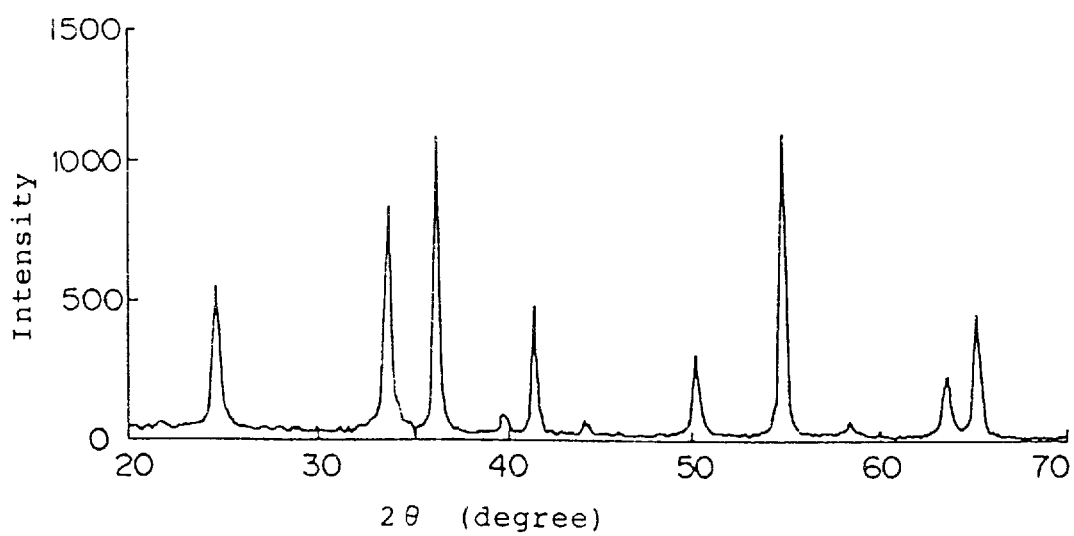

FIG. 1A shows an X-ray diffraction pattern of the chromium oxide prepared above. FIG. 1B shows an X-ray diffraction pattern of crystalline chromium oxide. From the comparison of these two diffraction patterns, it is understood that chromium oxide prepared in this Example was amorphous since FIG. 1A has no peak.

Using the amorphous chromium oxide catalyst, the fluorination of 133a was carried out under the following conditions:

Molar ratio (HF:133a): 9:1

Reaction temperature: 350° C.

Contact time: 0.5 (gsec/Nml)

(A ratio of a catalyst weight W to a flow rate F). The catalytic activity was 26.9%.

Comparative Example 1

In the same manner as in Example 1 but changing the precipitation conditions (a 5.7 wt. % aqueous solution of chromium nitrate (255 Kg), 10% aqueous ammonia (38 Kg) and the addition time of 9 minutes 45 seconds), a catalyst was prepared. Chromium hydroxide and chromium oxide had the following properties:

Chromium hydroxide

Powder density: 1.19 g/ml

Pellet strength: 93 kg/cm$^2$

Specific surface area: 79 m$^2$/g

Chromium oxide

Specific surface area: 126 m$^2$/g 133a was fluorinated in the same manner as in Example 1 but using above chromium oxide. The catalytic activity was 7.4%.

EXAMPLE 2

A catalyst was prepared as follows:

To a 5.7 wt. % aqueous solution of chromium nitrate (25.5 Kg), 10% aqueous ammonia (3.8 Kg) was added at 50° C. Then, a catalyst was prepared in the same manner as in Example 1.

Chromium hydroxide and chromium oxide had the following properties:

Chromium hydroxide

Powder density: 0.67 g/ml

Pellet strength: 178 kg/cm$^2$

Specific surface area: 141 m$^2$/g

Chromium oxide

Specific surface area: 221 m$^2$/g

When 133a was fluorinated at a molar ratio of 9:1, a reaction temperature of 350° C. and a contact time of 0.5, the catalytic activity was 17.3%.

When 133a was fluorinated at a molar ratio of 1:1, a reaction temperature of 350° C. and a contact time of 0.4, the catalyst life was 115 hours.

Comparative Example 2

In the same manner as in Example 2 but changing a precipitation temperature to 33° C., a catalyst was prepared. Chromium hydroxide and chromium oxide had the following properties:

Chromium hydroxide

Powder density: 0.53 g/ml

Pellet strength: 303 kg/cm$^2$

Specific surface area: 134 m$^2$/g

Chromium oxide

Specific surface area: 154 m$^2$/g 133a was fluorinated in the same manner as in Example 2 but the using above chromium oxide. The catalytic activity was 16.5% and the catalyst life was 89 hours.

EXAMPLE 3

To a 5.9 wt. % aqueous solution of chromium chloride (16.3 Kg), 10% aqueous ammonia (3.2 Kg) was added at 50° C. Then, a catalyst was prepared in the same manner as in Example 1. Chromium hydroxide and chromium oxide had the following properties:

Chromium hydroxide

Powder density: 0.62 g/ml

Pellet strength: 246 kg/cm$^2$

Specific surface area: 158 m$^2$/g

Chromium oxide

Specific surface area: 228 m$^2$/g

When 133a was fluorinated at a molar ratio of 9:1, a reaction temperature of 350° C. and a contact time of 0.5, the catalytic activity was 19.2%.

When 133a was fluorinated at a molar ratio of 1:1, a reaction temperature of 350° C. and a contact time of 0.4, the catalyst life was 106 hours.

Comparative Example 3

In the same manner as in Example 3 but changing a precipitation temperature to 33° C., a catalyst was prepared. Chromium hydroxide and chromium oxide had the following properties:

Chromium hydroxide

Powder density: 0.41 g/ml

Pellet strength: 220 kg/cm$^2$

Specific surface area: 48 m$^2$/g

Chromium oxide

Specific surface area: 122 m$^2$/g 133a was fluorinated in the same manner as in Example 3 but using above chromium oxide. The catalytic activity was 6.7% and the catalyst life was 80 hours.

EXAMPLE 4

Using the same catalyst as prepared in Example 2 except that the catalyst was used in the pellet form, 133a was fluorinated at a molar ratio of 4:1, a reaction temperature of 350° C. under one atm. at a conversion of 20%. The selectivity was 91.2%, the space velocity (SV) was 4557/hr, and the throughput was 1078 g/liter-catalyst/hr.

Comparative Example 4

In the same manner as in Example 4 but using a non-supported type chromium oxide (disclosed in Example 1 of GB 1 589 924 or corresponding Japanese Patent Kokai Publication No. 105404/1978), 133a was fluorinated. The selectivity was 91%, SV was 500/hr and the throughput was 82.9 g/liter-catalyst/hr.

EXAMPLE 5

Using the same catalyst as prepared in Example 2 except that the catalyst was used in the pellet form, 133a was fluorinated at a molar ratio of 4.6:1, a reaction temperature of 330° C. under one atm. at a conversion of 20.3%. The selectivity was 95.7%, SV was 2250/hr, and the throughput was 483 g/liter-catalyst/hr.

Comparative Example 5

133a was fluorinated in the same manner as in Example 5 but using a supported type chromium oxide which is disclosed in Example 1 of WO89/10341 and prepared as follows:

In a solution of $CrCl_3.6H_2O$ (191.5 g) in water (132 ml), activated alumina (400 g) was dipped. Then, alumina was dried at 90° C. on a water bath, at 110° C. in an air for 3 hours and at 400° C. for 3 hours. A calculated composition of the catalyst was 12% by weight of $Cr_2O_3$ and 88% by weight of $Al_2O_3$. The catalyst was fluorinated under the following conditions:

Hydrogen fluoride: 25 to 100% by mole
Temperature: 250° to 420° C.
SV: 400/hr
Time: 15 hours.

The selectivity was 94.3%, SV was 101/hr and the throughput was 15.6 g/liter-catalyst/hr.

EXAMPLE 6

Figure 2:
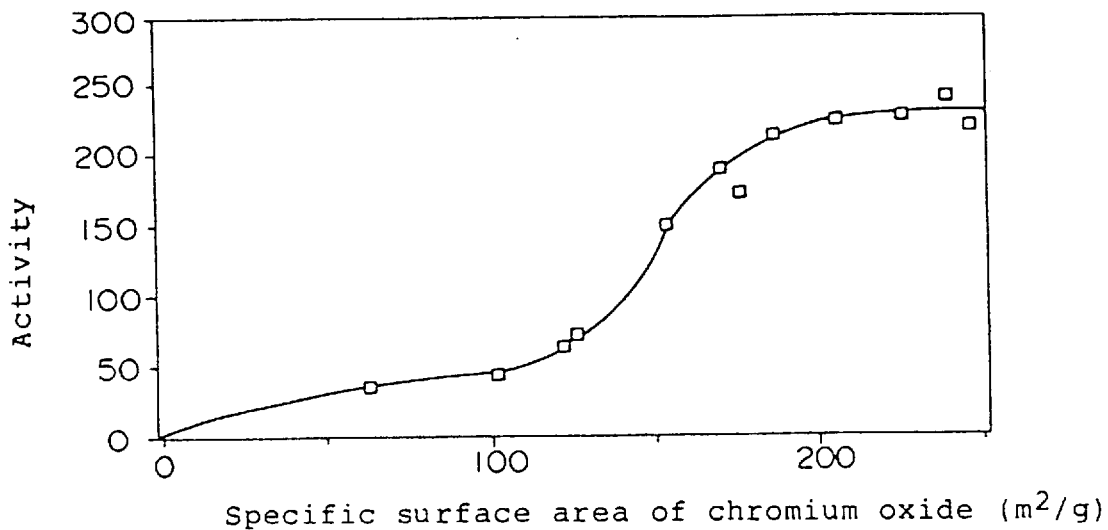
FIGS. 2, 3 and 4 compare the catalytic activities of the various chromium catalysts disclosed.

Using pellet-form chromium oxide catalysts having different specific surface areas, 133a was fluorinated with hydrogen fluoride at a molar ratio of 9:1, a reaction temperature of 350° C. and a contact time of 0.5, and a catalytic activity was measured. The results are shown in FIG. 2.

In this Example and subsequent Examples, the catalytic activity is defined as a reaction speed at 350° C. The catalytic activity is expressed as a relative value.

EXAMPLE 7

Figure 3:
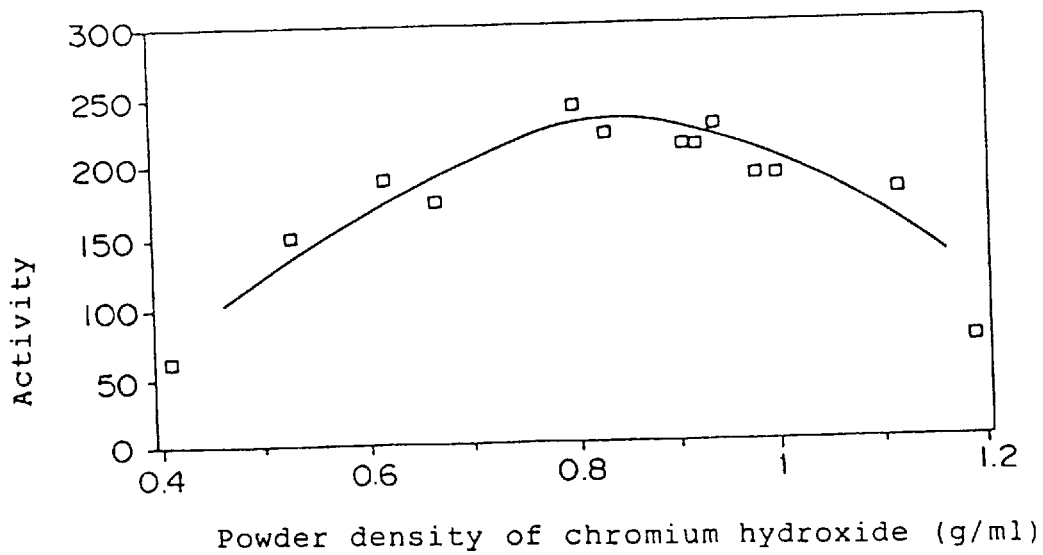

Using pellet-form chromium oxide catalysts which were prepared from chromium hydroxide having different powder densities, 133a was fluorinated with hydrogen fluoride at a molar ratio of 9:1, a reaction temperature of 350° C. and a contact time of 0.5, and a catalytic activity was measured. The results are shown in FIG. 3.

EXAMPLE 8

Figure 4:
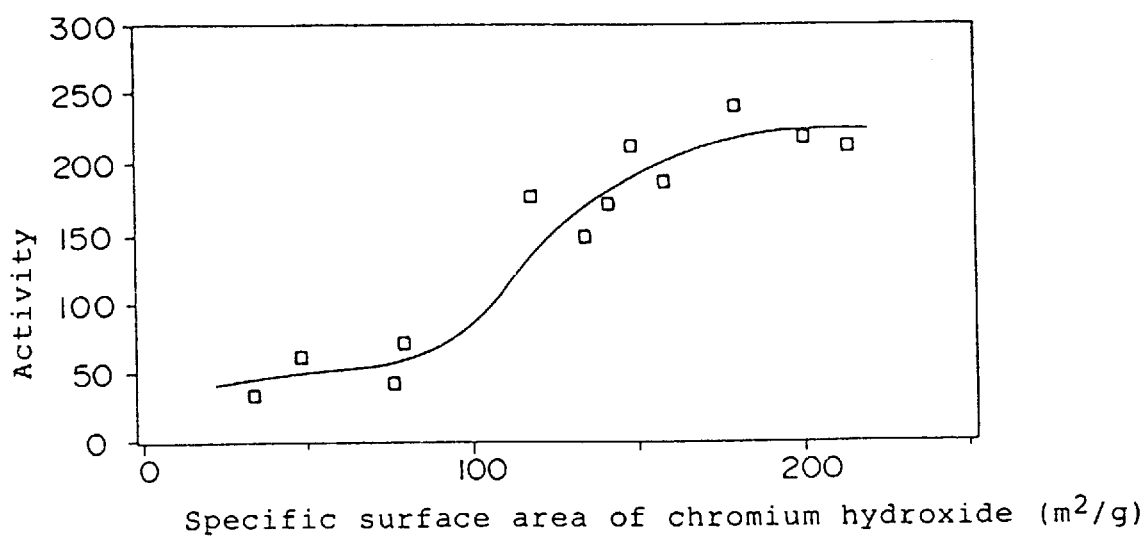

Using pellet-form chromium oxide catalysts which were prepared from chromium hydroxide having different specific surface areas, 133a was fluorinated with hydrogen fluoride at a molar ratio of 9:1, a reaction temperature of 350° C. and a contact time of 0.5, and a catalytic activity was measured. The results are shown in FIG. 4.

In Example 9, perchloroethylene was fluorinated and in Example 10, dichloromethane was fluorinated.

EXAMPLE 9

In a Hasteloy C made reactor tube having an inner diameter of 15 mm, the catalyst which was prepared in the same manner as in Example 2 and had a particle size of 300 to 600 $\mu$m (7 g) was charged. Through the reactor tube, hydrogen fluoride and perchloroethylene flowed at flow rates of 190 Nml/min. and 19 Nml/min., respectively and reacted at 350° C.

The conversion of perchloroethylene was 92%, and selectivities of 1,1-dichloro-2,2,2-trifluoroethane, 1-chloro-1,2,2,2-tetrafluoroethane and pentafluoroethane were 20%, 28% and 44%, respectively.

EXAMPLE 10

In a Hasteloy C made reactor tube having an inner diameter of 15 mm, the catalyst which was prepared in the same manner as in Example 2 and in the pellet form (4 g) was charged. Through the reactor tube, hydrogen fluoride and dichloromethane were flowed at flow rates of 360 Nml/min. and 90 Nml/min., respectively and reacted at 275° C.

The conversion of dichloromethane was 62%, and selectivities of fluorochloromethane and difluoromethane were 20% and 80%, respectively.

What is claimed is:

1. A method for preparing a fluorination catalyst which consists essentially of the steps of:

mixing an aqueous solution of a chromium salt with aqueous ammonia to precipitate chromium hydroxide, drying the precipitated chromium hydroxide, sintering the dried chromium hydroxide to obtain chromium oxide having a specific surface area of 170 $m^2/g$ to 300 $m^2/g$, and fluorinating the chromium oxide to obtain the chromium oxide catalyst having a fluorine content of at least 8%.

2. The method according to claim 1, wherein the chromium hydroxide is sintered to produce amorphous chromium oxide.

3. The method according to claim 1, wherein the chromium oxide obtained by sintering dried chromium hydroxide has a specific surface area of at least 180 $m^2/g$.

4. The method of claim 1, wherein the chromium oxide obtained by sintering dried chromium hydroxide has a specific surface area of from 180 $m^2/g$ to 280 $m^2/g$, and wherein the precipitated chromium hydroxide is dried and pelletized.

5. The method of claim 4, wherein the chromium oxide obtained by sintering chromium hydroxide has a specific surface area of 200 $m^2/g$ to 260 $m^2/g$.

6. The method of claim 4, wherein said pelletized chromium hydroxide is sintered at a temperature of from 380° C. to 460° C.

7. The method of claim 1, wherein said chromium hydroxide is dried and pelletized at a temperature of 70° C. to 200° C. and said pelletized chromium hydroxide is sintered at a temperature of 380° C. to 460° C.

8. The method of claim 1, wherein the chromium oxide is fluorinated to obtain the chromium oxide catalyst having a fluorine content of at least 15%.

* * * * *